(12) United States Patent
Haley

(10) Patent No.: US 7,935,537 B2
(45) Date of Patent: May 3, 2011

(54) SAMPLE PREPARATION DEVICE AND METHOD

(75) Inventor: Cecelia Haley, Northville, MI (US)

(73) Assignee: HandyLab, Inc., Ann Arbor, MI (US)

( * ) Notice: Subject to any disclaimer, the term of this patent is extended or adjusted under 35 U.S.C. 154(b) by 0 days.

(21) Appl. No.: 12/834,782

(22) Filed: Jul. 12, 2010

(65) Prior Publication Data

US 2010/0279430 A1    Nov. 4, 2010

Related U.S. Application Data

(62) Division of application No. 11/078,183, filed on Mar. 11, 2005, now Pat. No. 7,763,209.

(60) Provisional application No. 60/551,787, filed on Mar. 11, 2004.

(51) Int. Cl.
*G01N 1/00* (2006.01)
*C12M 1/00* (2006.01)
*B01L 3/02* (2006.01)

(52) U.S. Cl. .................... 436/174; 435/283.1; 422/501

(58) Field of Classification Search .................. 436/174; 435/283.1; 422/501
See application file for complete search history.

(56) References Cited

U.S. PATENT DOCUMENTS

| | | | |
|---|---|---|---|
| 6,010,627 A * | 1/2000 | Hood, III | 210/321.6 |
| 6,905,612 B2 * | 6/2005 | Dorian et al. | 210/806 |
| 2004/0063217 A1 * | 4/2004 | Webster et al. | 436/180 |

\* cited by examiner

*Primary Examiner* — Lore Jarrett
(74) *Attorney, Agent, or Firm* — Knobbe Martens Olson & Bear LLP

(57) ABSTRACT

A sample preparation device for reducing a concentration of one or more concomitant components of a sample and/or increasing a concentration of one or more desired sample components is described.

20 Claims, 1 Drawing Sheet

SAMPLE PREPARATION DEVICE AND METHOD

CROSS-REFERENCE TO RELATED APPLICATIONS

This application is a divisional of copending U.S. application Ser. No. 11/078,183, titled "Sample Preparation Device and Method," filed Mar. 11, 2005, which claims the benefit of U.S. Provisional Application No. 60/551,787, filed Mar. 11, 2004. The disclosures of all the above-referenced applications, publications, and patents are considered part of the disclosure of this application, and are incorporated by reference herein in their entirety.

BACKGROUND OF THE INVENTION

1. Field of the Invention

The invention relates to a sample preparation device as well as to related methods.

2. Description of the Related Art

One of the common difficulties in performing bio-assays is preparing a sample for testing. Raw samples can be obtained from a bodily fluid, bodily waste, or from a swab that is subsequently placed in a buffer solution to release collected cells, DNA, and varying amounts of extraneous matter collected during the swabbing. Current sample preparation techniques can be expensive, labor intensive, time consuming, and can rely heavily on human participation.

Preparation of raw samples for testing typically includes clean up steps, such as forcing the sample through various sizes and types of filters to trap, isolate, screen, or sort out particles that range down to micron and sub-micron sizes. During preparation, samples can be contaminated or otherwise rendered unusable due to handling or simple human error. Proper sample concentration and clean-up reduces clogging especially when used with micro-scale structures.

The recent arrival of point of care devices for use in clinics and doctors' offices has increased the need for a simple, yet robust preparation device that a non-technician can use to perform the critical step of sample preparation at the 'point of care.' This creates an intense need for a device to simplify sample preparation and concentration while maintaining the integrity of the sample.

Current sample preparation and concentration methods usually involve a syringe and a single size filter for each clean up step. Such filters utilize a single direction of fluid flow, and are typically operated using the injection stroke of a syringe to filter out large particles. The sample is filtered through different, successively smaller filters such as by fitting the filters to a different syringe. Each time the filter is changed, technician time increases and the possibility of sample contamination also increases.

SUMMARY

The present invention relates to a sample preparation device as well as to related systems and methods. In general, the result of the sample preparation is to provide a processed sample having a reduced amount of concomitant components relative to an unprocessed sample and/or a processed sample that is enriched in one or more desired sample components relative to an unprocessed sample.

In some embodiments, the invention relates to a device that includes distinct passages having different (e.g., separate) intake/outflow openings and valves. Sample can pass in only one direction along each passage.

In some embodiments, the device is configured to process a sample using both the intake and output motions of a syringe. For example, the intake motion can draw a sample through a first passage of the device and the output motion of the syringe can expel the sample through a second, different passage of the device. This can be performed, for example, without detaching the device from the syringe.

In some embodiments, one or more of the passages can filter the sample and/or one or more of the passages can enrich the sample.

In some embodiments, the device includes an integral pressure device such as a syringe as opposed to being designed for use with a stand-alone pressure device.

The device can include fittings that are compatible with standard syringes, and can be disposed of with standard biomedical waste. The device allows safe injection of samples into micro-fluidic devices without overwhelming such microfluidic devices with excessive pressure.

In some embodiments, a sample processing device includes a body defining a first passage configured to allow passage of fluid in only a first direction with respect to the body and a second passage configured to allow passage of fluid in only a second, different direction with respect to the body. A fluid retention member is disposed along at least one of the first and second passages. The fluid retention member is configured to retain fluid that passes along the first and second passage so that the amount of fluid that exits the passage is less than the amount of fluid that entered the passage.

DETAILED DESCRIPTION

Figure 1:
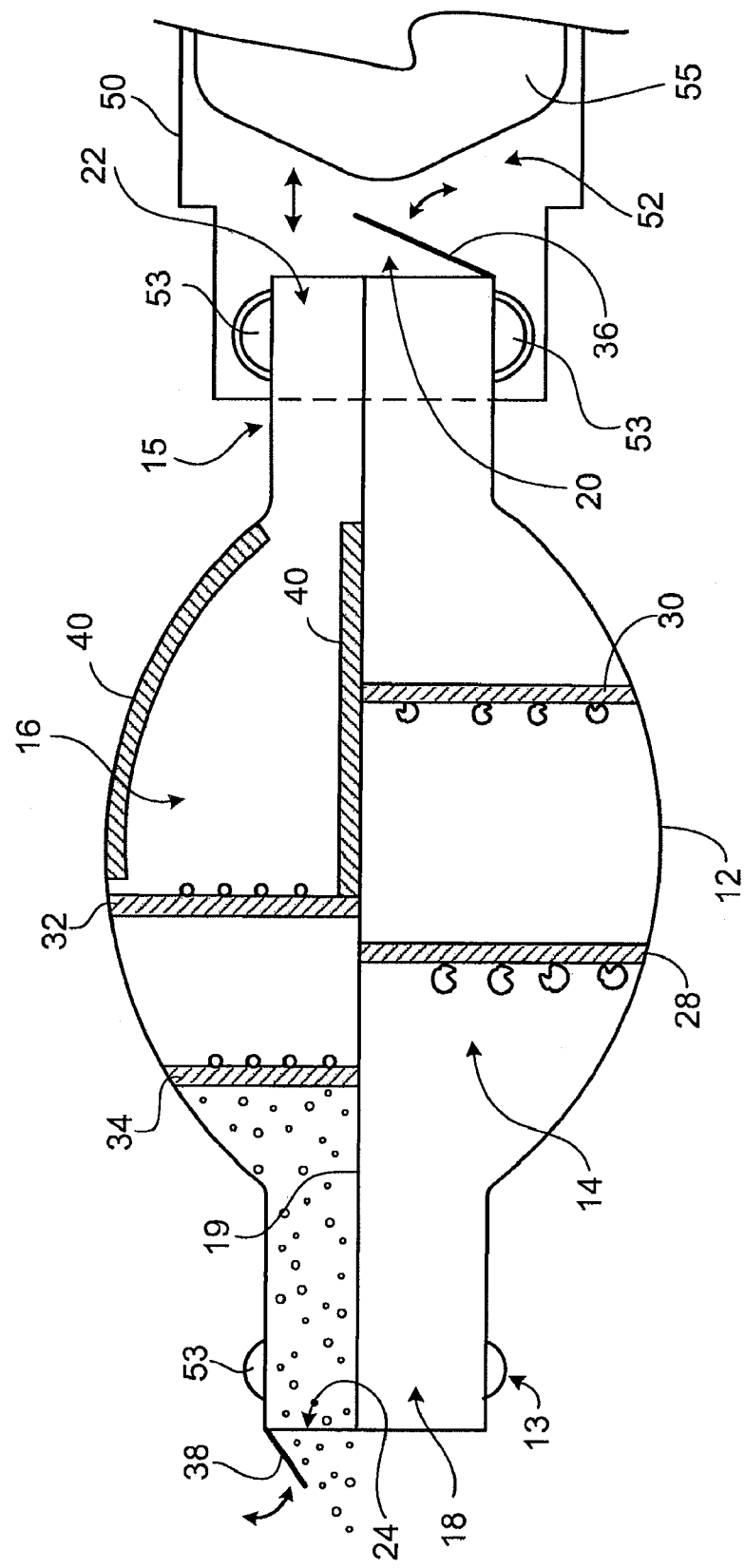
FIG. 1 shows an embodiment of a sample preparation device.

Referring to FIG. 1, a sample preparation device 10 is configured to process a sample including (a) at least one desired sample component, e.g., one or more polynucleotides or other biological material, one or more cells, viruses, or other microorganisms and, typically, (b) one or more concomitant components, e.g., one or more polynucleotides or other biological material, cells, viruses, or other microorganisms, tissue, particulates and the like. The desired and concomitant components of the sample can be entrained in a fluid (e.g., a liquid). Typical samples include blood and samples generated from tissue swabs and other tissue samples such as by combining a tissue or cell sample with buffer. Device 10 processes such samples to provide a processed sample including: (a) a reduced amount (e.g., none) of concomitant components (if present in the original sample) relative to the amount of a desired sample component(s), (b) a processed sample enriched in the desired sample component(s) relative to an amount of fluid entraining the desired sample component, or (c) a processed sample having both of these properties.

Device 10 includes a body 12 defining a first end 13, a second end 15, a first passage 14 and a second passage 16. Body 12 is shown as bulb shaped but may have other configurations (e.g., cylindrical, rectangular, or onion shaped). First passage 14 has a first opening 18 and a second opening 20. Second passage 16 has a first opening 22 and a second opening 24. In general, first passage 14 provides a passage for the intake of a sample by device 10, whereas the second passage 16 provides a passage for the output of a processed sample by device 10. A wall 19 isolates first and second passages 14, 16 from one another such that desired sample components and, generally, other material cannot pass between the passages except via openings thereof.

First and second ends 13, 15 of device 10 include a fitting 53 (e.g., a Luer loc fitting) so that device 10 can be coupled to other devices (e.g., to a syringe, a source of sample, or to another processing device).

Second opening 20 of first passage 14 includes a valve 36 configured to allow fluid and particles to exit first passage 14 via second opening 20 and to limit or prevent entry of fluid and particles to first passage 14 via second opening 20. Second opening 24 of second passage 16 includes a valve 38 configured to allow fluid to exit second passage 16 via second opening 24 and to limit or prevent entry of fluid and particles to second passage 16 by second opening 24. Valves 36 and 38 are generally one-way valves.

In use, a vacuum source (e.g., a syringe 50) is mated with second opening 20 of first passage 14 and first opening 22 of second passage 16. The first end 18 of first passage 14 and the second opening 24 of the second passage 16 are contacted with a sample (e.g., a sample to be processed). A plunger 55 of syringe 50 is withdrawn to apply a reduced pressure to second opening 20 of first passage 14 and to first opening 22 of second passage 16. Valve 38 at second opening 24 of second passage 16 closes to prevent sample from entering the second passage. Sample is drawn into first passage 14 through first opening 18, drawn along first passage 14, and then withdrawn from first passage 14 through second opening 20 and valve 36. The exiting sample typically enters a reservoir of the vacuum source (e.g., a barrel 52 of syringe 50).

The plunger of syringe 50 is then depressed to apply pressure to sample within barrel 52. Valve 36 closes to prevent material from reentering first passage 14. Sample is pushed into second passage 16 through first opening 22, pushed along second passage 16, and pushed from second opening 24 through valve 38 to exit device 10. Second passage 16 can have smaller dimensions (e.g., a smaller radial cross section) than first passage 14. The smaller cross section can reduce the force required to move material through the second passage.

Sample is typically subjected to at least one processing step (e.g., enrichment of desired sample components and/or concomitant component reduction or removal as by filtration) while traveling through each of the first and second passages.

In embodiments configured to at least reduce the relative amount of concomitant sample components, device 10 can include at least one and optionally a plurality of retention elements configured to retain concomitant components of the sample while allowing passage of desired sample components. For example, retention elements, e.g., filters 28, 30, 32, and 34, can retain particles having a size greater than the size of the desired sample component(s). Filters 28, 30, 32, and 34 may be, for example, a torturous path filter or a screen or mesh type filter. The type of filter in each device depends upon the components of the sample and the filtration requirements. Filters 28, 30, 32, and 34 generally retain particles of decreasing size. First sample passage 14 can have greater dimensions, e.g., a greater radial cross section, than second passage 16 to allow filters disposed along first passage 14 to have a greater surface area than if the passages had the same size cross sections.

It should be noted that filters 28, 30, 32, and 34 may also (or alternatively) be configured as adsorptive filters configured to adsorb and/or bind one of the desired sample component(s) and concomitant sample components to a greater extent than the other. Filters 28, 30, 32, and 34 can be formed of any material compatible with samples to be processed.

In embodiments configured to provide a processed sample enriched in the desired sample component(s) relative to the amount of fluid, device 10 can include a fluid retention member 40 configured to retain fluid of the sample to a greater extent than the one or more desired sample components. For example, retention member 40 can comprise a porous network capable of retaining a given amount of fluid. The porous network can be hydrophilic. The porous network can comprise a ceramic medium, such as moderately or hard fired alumina, or a porous glass medium. Other suitable materials include polymers, e.g., polytetrafluoroethylene or polyethylene, configured as porous networks.

The void volume of the porous medium can be at least 15%, at least 25%, or at least 30% of the porous network. Retention member 40 is generally configured to minimize retention of the desired sample component. For example, the pore size can be selected to be smaller than the size of the desired sample component. Retention member 40 can include a layer, e.g., a coating, configured to minimize association, e.g., adsorption, by the retention member 40 of the desired sample component.

As an alternative to or in combination with a porous network, retention member 40 can comprise an absorptive medium configured to retain water by absorption such as through solvation. Preferred absorptive media comprise a plurality of chemical constituents, e.g., hydroxyl groups, organic acid groups, hydrogen bonding groups, ionic groups, and the like, with which water can associate. Exemplary polymers include acrylates, e.g., sodium polyacrylate, cellulose, e.g., carboxymethylcellulose and hydroxyethylcellulose, and acrylamide polymers. The absorptive medium can comprise a substantial amount of cross linked material.

In some embodiments, device 10 is configured to receive a sample having a liquid volume of at least about 500 microliters (e.g., at least about 1000 microliters, at least about 2000 microliters, at least about 5000 microliters) into opening 18 of first passage 14. In some embodiments, device 10 is configured to receive a sample having a liquid volume of no more than about 750 microliters (e.g., no more than about 1500 microliters, no more than about 2500 microliters, no more than about 10000 microliters) into opening 18 of first passage 14.

In some embodiments, device 10 is configured to provide (e.g., from second opening 24 of second passage 16) a processed sample having a liquid volume of no more than about 90% (e.g., no more than about 80%, no more than about 65%, no more than about 50%, no more than about 25%) of the liquid volume of the sample introduced into opening 18 of first passage 14. At least some (e.g., most or essentially all) of the remaining liquid is retained by one or more retention members of device 10. Because the one or more retention members retain liquid preferentially to the desired sample material, the processed sample can be enriched in the desired sample material by at least about 10% (e.g., at least about 20%, at least about 35%, at least about 50%, at least about 75%, or more) as compared to the sample introduced to first opening 18 of first passage 14.

Device 10 can be formed of material including but not limited to metal, polymer, e.g., plastic, polytetrafluoroethylene, nylon, or any other polymer, co-polymer or synthetic type material that is sufficiently inert with respect to desired sample materials. Components of device 10, e.g., valves and filters as discussed below, can be secured using, e.g., laser or ultrasonic welding, adhesives including epoxies, solder, heat staking, press fitting, and the like.

Other embodiments are within the claims.

What is claimed is:

1. A method for processing a sample, comprising:
   (i) contacting a sample with (a) a first opening of a first passage, the first passage including a second opening and a valve configured to allow material from the sample to pass only from the first opening of the first passage and into a reservoir of a vacuum source, and (b) a second opening of a second passage, the second passage including a first opening and a valve configured to allow material from the sample to pass only from the reservoir and into the first opening of the second passage toward the second opening of the second passage, wherein a wall isolates the first and second passages from one another such that material cannot pass between the first and second passages except via the respective first and second openings thereof;

(ii) modifying a pressure differential between the first opening of the first passage and the second opening of the first passage so that sample passes into the first passage through its first opening and exits the first passage through its second opening and into the reservoir of the vacuum source, wherein material that exits the first passage and into the reservoir comes into liquid communication with the first opening of the second passage;

(iii) modifying a pressure differential between the first opening of the second passage and the second opening of the second passage so that at least some of the material from the sample that has exited the first passage passes into the second passage through its first opening and exits the second passage through its second opening.

2. The method of claim 1, wherein (ii) modifying comprises decreasing a pressure acting on the second opening of the first passage.

3. The method of claim 2, wherein (ii) modifying comprises simultaneously decreasing a pressure acting on the first opening of the second passage, wherein the valve of the second passage substantially prevents material from entering the second opening of the second passage.

4. The method of claim 1, wherein (iii) modifying comprises increasing a pressure acting on the first opening of the second passage.

5. The method of claim 4, wherein (iii) modifying comprises simultaneously increasing a pressure acting on the second opening of the first passage, wherein the valve of the first passage substantially prevents material from entering the second opening of the first passage.

6. The method of claim 1, wherein the sample comprises sample particles entrained in a liquid, and the method further comprises retaining at least some of the liquid that passes along at least one of the first passage and the second passage so that a concentration of particles that exits the second opening of the second passage is greater than a concentration of particles that enters the first opening of the first passage.

7. The method of claim 6, wherein the concentration of particles that exits the second opening of the second passage is at least 20% greater than the concentration of particles that enters the first opening of the first passage.

8. The method of claim 6, wherein the concentration of particles that exits the second opening of the second passage is at least 10% greater than the concentration of particles that enters the first opening of the first passage.

9. The method of claim 1, wherein the sample comprises particles of a first type and particles of a second type entrained in a liquid, and the method further comprises binding at least some of the particles of the first type that pass along at least one of the first passage and the second passage while allowing passage of particles of the second type to pass without substantial binding.

10. The method of claim 9, wherein the particles of the first type are larger than the particles of the second type.

11. A method for processing a sample, comprising:
contacting a sample with a first end of a sample processing device, the device comprising a second end securable to a vacuum source, the device further comprising a first passage and a second passage, the first passage and the second passage extending between the first end and the second end and each comprising a respective first opening and a respective second opening, wherein a wall isolates the first and second passages from one another such that material cannot pass between the first and second passages except via the respective first and second openings thereof;

drawing material from the sample into the device such that the material passes only in a first direction from the first opening of the first passage toward the second opening of the first passage and into a reservoir of the vacuum source;

moving the material out of the reservoir such that the material passes only in a second and opposite direction from the reservoir into the first opening of the second passage toward the second opening of the second passage; and expelling at least some of the material drawn into the device through the first opening of the first passage out of the device through the second opening of the second passage.

12. The method of claim 11, wherein the second opening of the first passage comprises a first valve, and drawing material from the sample into the device comprises applying reduced pressure to the second opening of the first passage and opening the first valve.

13. The method of claim 12, wherein the second opening of the second passage comprises a second valve, and drawing material from the sample into the device further comprises closing the second valve to substantially prevent material from entering the second opening of the second passage.

14. The method of claim 13, wherein moving the material out of the reservoir comprises applying pressure to the material in the reservoir and opening the second valve.

15. The method of claim 14, wherein moving the material out of the reservoir further comprises closing the first valve to substantially prevent material from entering the second opening of the first passage.

16. The method of claim 11, wherein the sample comprises sample particles entrained in a liquid, and the method further comprises retaining at least some of the liquid that passes along at least one of the first passage and the second passage so that a concentration of particles that exits the second opening of the second passage is greater than a concentration of particles that enters the first opening of the first passage.

17. The method of claim 16, wherein the concentration of particles that exits the second opening of the second passage is at least 20% greater than the concentration of particles that enters the first opening of the first passage.

18. The method of claim 16, wherein the concentration of particles that exits the second opening of the second passage is at least 10% greater than the concentration of particles that enters the first opening of the first passage.

19. The method of claim 11, wherein the sample comprises particles of a first type and particles of a second type entrained in a liquid, and the method further comprises binding at least some of the particles of the first type that pass along at least one of the first passage and the second passage while allowing particles of the second type to pass without substantial binding.

20. The method of claim 19, wherein the particles of the first type are larger than the particles of the second type.

* * * * *